United States Patent [19]

Hurt

[11] 4,029,774
[45] June 14, 1977

[54] O,S-DIALKYL O-PHENYLTHIO-PHENYL PHOSPHOROTHIOLATES/PHOSPHORODITHIOATES AND THEIR DERIVATIVES AND PESTICIDAL USE

[75] Inventor: William S. Hurt, Collegeville, Pa.

[73] Assignee: Rohm and Haas Company, Philadelphia, Pa.

[22] Filed: May 12, 1975

[21] Appl. No.: 576,836

Related U.S. Application Data

[63] Continuation-in-part of Ser. No. 483,190, June 26, 1974, abandoned.

[52] U.S. Cl. .............................. 424/216; 260/949
[51] Int. Cl.[2] ................... A01N 9/36; C07F 9/18
[58] Field of Search ................ 260/949; 424/216

[56] References Cited

UNITED STATES PATENTS

| | | | |
|---|---|---|---|
| 3,042,703 | 7/1962 | Schegk et al. ............. | 260/949 |
| 3,153,663 | 10/1964 | Sirrenberg et al. ......... | 260/949 X |
| 3,825,636 | 7/1974 | Kishino et al. ............. | 260/949 X |
| 3,839,511 | 10/1974 | Kishino et al. ............. | 260/949 X |
| 3,898,305 | 8/1975 | Beriger et al. ............. | 260/949 X |

FOREIGN PATENTS OR APPLICATIONS 1,193,036  5/1965  Germany ................ 260/949

*Primary Examiner*—Richard L. Raymond
*Attorney, Agent, or Firm*—Betty A. Narducci; George W. F. Simmons; Carl A. Castellan

[57] ABSTRACT

This invention relates to novel organophosphorothiolates and phosphorodithioates of the formula:

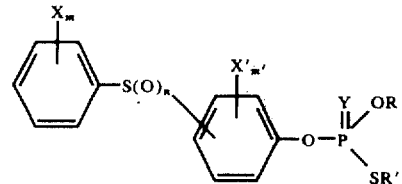

wherein
 Y is oxygen or sulfur;
 R is $(C_1-C_4)$ alkyl;
 R' is $(C_3-C_8)$ alkyl;
 X is halogen, nitro, trifluoromethyl, $(C_1-C_5)$ alkyl or $(C_1-C_5)$ alkoxy;
 X' is halogen, trifluoromethyl, $(C_1-C_5)$ alkyl or $(C_1-C_5)$ alkoxy;
 m and m' are the same or different and are integers from 0 to 3;

to compositions containing them, and to methods of using them to control pests.

26 Claims, No Drawings

O,S-DIALKYL O-PHENYLTHIO-PHENYL PHOSPHOROTHIOLATES/PHOSPHORODITHIOATES AND THEIR DERIVATIVES AND PESTICIDAL USE

This application is a continuation-in-part of U.S. Ser. No. 483,190, filed June 26, 1974, now abandoned.

The present invention relates to novel organophosphorothiolates and phosphorodithioates, having pesticidal activity, especially acaricidal and insecticidal activity, to compositions containing them, and to methods of using them to control various harmful pests. In addition to possessing outstanding pesticidal activity, compounds of the present invention possess a combination of desirable characteristics not possessed by known organophosphorus pesticides. These characteristics include activity against organophosphorus resistant species, residual activity, low toxicity to warm-blooded animals and low phytotoxicity for economically important plant species.

These novel compounds can be represented by the formula:

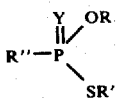

wherein Y is oxygen or sulfur; R is $(C_1-C_4)$ alkyl; R' is $(C_3-C_6)$ alkyl; and R'' is a group of the formula:

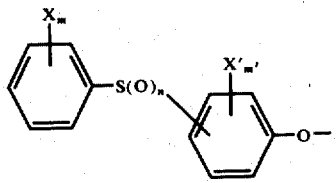

wherein
X is halogen, nitro, trifluoromethyl, $(C_1-C_5)$ alkyl of $(C_1-C_5)$ alkoxy;
X' is halogen, trifluoromethyl, $(C_1-C_5)$ alkyl of $(C_1-C_5)$ alkoxy;
$m$ and $m'$ are the same or different and are integers from 0 to 3; and
$n$ is an integer from 0 to 2.

As used in the specification and claims, the terms "alkyl" and "alkoxy" are intended to include branched chain as well as straight chain alkyl and alkoxy groups. Representative alkyl groups include methyl, ethyl, n-propyl, sec-butyl, isobutyl, pentyl, neopentyl, 2-methyl-pentyl, n-hexyl, and the like. Representative alkoxy groups include methoxy, ethoxy, propoxy, sec-butoxy, pentoxy and the like.

The organophosphorothiolates and phosphorodithioates described above can exist in their isomeric forms, wherein the phenylthio, phenylsulfinyl or phenylsulfonyl group is attached to the benzene ring in a position which is ortho, meta or para to the point of attachment of the phosphorothiolate or phosphorodithioate group.

The preferred compounds of this invention possess particularly enhanced acaricidal, especially miticidal, and insecticidal activity and have the formula:

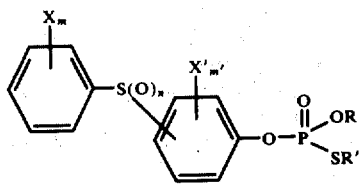 (I)

wherein
R is $(C_1-C_4)$ alkyl, preferably ethyl;
R' is a $(C_3-C_5)$ alkyl group having the formula:

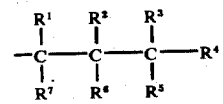

wherein
$R_1-R^7$ are individually hydrogen, methyl or ethyl, preferably hydrogen;
X is halogen, preferably chlorine or fluorine; nitro; or methyl;
X' is halogen, preferably chlorine or bromine; methyl; or methoxy;
$m$ is an integer from 0 to 2;
$m'$ is an integer from 0 to 1;
$n$ is an integer from 0 to 2, preferably zero, and the phenylthio, phenylsulfinyl or phenylsulfonyl group is attached to the benzene ring at a position which is ortho or para, preferably para, to the point of attachment of the phosphorothiolate group.

Typical compounds within the scope of this invention include:
O-methyl O-(4-phenylthiophenyl) S-n-propyl phosphorothiolate
S-n-hexyl O-methyl O-(4-phenylthiophenyl) phosphorothiolate
S-n-butyl O-ethyl O-(4-phenylthiophenyl) phosphorothiolate
O-ethyl S-isobutyl O-(4phenylthiophenyl) phosphorothiolate
S-sec-butyl O-ethyl O-(4-phenylthiophenyl) phosphorothiolate
O-ethyl S-n-pentyl O-(4-phenylthiophenyl) phosphorothiolate
O-isopropyl O-(4-phenylthiophenyl) S-n-propyl phosphorothiolate
O-n-butyl O-(4-phenylthiophenyl) S-n-propyl phosphorothiolate
O-ethyl O-(2-phenylthiophenyl) S-n-propyl phosphorothiolate
O-ethyl O-[3-(4'-methoxy)phenylthiophenyl] S-n-propyl phosphorothiolate
O-ethyl O-[3-methyl-4-(4'-nitro)phenylthiophenyl] S-n-propyl phosphorothiolate
O-[3-butoxy-4-(4'-bromo)phenylthiophenyl] O-n-propyl S-n-propyl phosphorothiolate
O-ethyl S-isobutyl O-[4-(2'-nitro)phenylthiophenyl] phosphorothiolate
O-ethyl S-isobutyl O-[4-(4'-trifluoromethyl)phenylthiophenyl] phosphorothiolate
O-[2-chloro-4-(4'-chloro)phenylthiophenyl] O-ethyl S-isobutyl phosphorothiolate
O-[2,6-dichloro-4-(4'-chloro)phenylthiophenyl] O-ethyl S-isobutyl phosphorothiolate O-[4-(3',4'-dichloro)phenylthiophenyl] O-ethyl S-isobutyl phosphorothiolate O-methyl S-n-propyl O-[2-(2',4', 6'-trichloro)phenylthiophenyl] phosphorothiolate O-ethyl O-[4-(4'-methyl)phenylthio-3-methylphenyl] S-n-propyl phosphorothiolate O-ethyl O-[2-methyl-4-phenylthiophenyl] S-n-propyl phosphorothiolate S-sec-butyl O-ethyl [4-(5'-chloro-3'-methyl)phenylthiophenyl] phosphorothiolate O-ethyl O-[4-(4'-fluoro)phenylthio-3-methylphenyl] S-isobutyl phosphorothiolate O-ethyl O-(2-phenylthio-3-trifluoromethylphenyl) S-n-propyl phosphorothiolate O-ethyl O-(4-phenylthio-3-trifluoromethylphenyl) S-n-propyl phosphorothiolate O-[4-(3'-chloro)phenylthio-3-ethylphenyl]-S-isopentyl O-methyl phosphorothiolate O-[4(4'-n-butyl)phenylthiophenyl] O-ethyl S-n-propyl phosphorodithioate O-ethyl O-(4-phenylsulfinylphenyl) S-n-propyl phosphorothiolate O-ethyl O-(3-phenylsulfinylphenyl) S-n-propyl phosphorthiolate O-ethyl O-[4-(4'-methyl)phenylsulfinylphenyl] S-n-propyl phosphorothiolae O-methyl O-[3-methyl-44(4'-nitro)phenylsulfinylphenyl] S-n-propyl phosphorothiolate O-ethyl O-(6-chloro-3-methyl-4-phenylsulfinylphenyl) S-n-propyl phosphorothiolate O-ethyl S-isobutyl O-(3,4,5-trimethyl-2-phenylsulfinylphenyl) phosphorothiolate O-[2-chloro-4-(4'-chloro)phenylsulfinyl phenyl] O-methyl S-n-propyl phosphorodithioate O-ethyl O-(4-phenylsulfonyl phenyl) S-n-propyl phosphorothiolate O-ethyl O-(2-phenylsulfonylphenyl)S-n-propyl phosphorothiolate S-isobutyl O-(3-,methoxy-4-phenylsulfonylphenyl9 O-methyl phosphorodithioate and the like.

The compounds of this invention can be prepared by reacting a phenol with an O,S-dialkylphosphorochloridothiolate or phosphorochloriododithioate. The general reaction can be represented by the following equation:

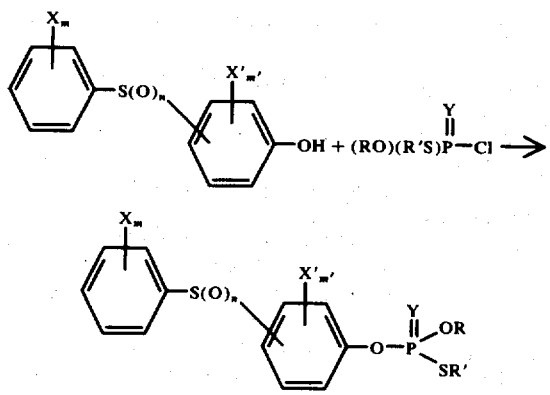

wherein Y, R, R', X, X', m, m' and n are as defined for Formula I.

An acid acceptor such as a tertiary amine or an alkali carbonate or hydroxide can be employed as a scavenger in the preparation. Representative acid acceptors include pyridine, trimethylamine, triethylamine, dimethylaniline, lithium carbonate, sodium hydroxide, potassium hydroxide and the like. Generally, an equimolar ratio of reactants is preferred but an excess of any of the reactants can be employed. While not required, the reaction is advantageously carried out in an inert organic solvent such as an aromatic hydrocarbon, halogenated aromatic hydrocarbon, aliphatic hydrocarbon, aliphatic ketone, aliphatic nitrile, ether solvent and the like. Suitable solvents include benzene, toluene, heptane, methylethyl ketone, acetone, diethyl ether, acetonitrile and dioxane. The reaction is generally conducted at a temperature range of about 0° to about 60° C.

In addition to the above procedure, the compounds of this invention can be prepared by reacting an alkali phenoxide with an O,S-dialkylphosphorochloridothiolate or phosphorochloridodithioate. This reaction can be represented by the following equation:

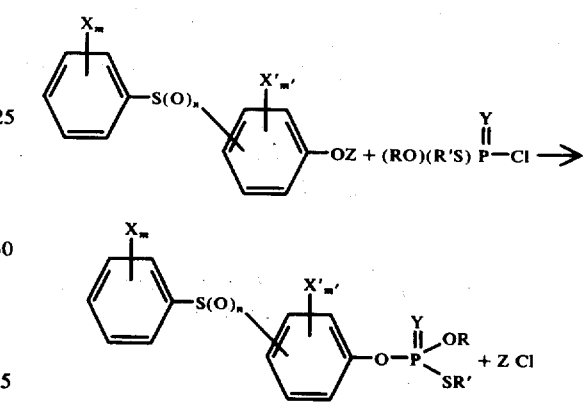

wherein Y, R, R', X, X', m, m' and n are as defined for Formula I and Z is an alkali metal.

Reaction conditions, including choice of solvents, temperature, and molar ratios correspond to the conditions described above for the reaction with a phenol, except that there is no need to employ an acid acceptor in this reaction.

The phenolic starting materials are known in the literature or are prepared by adaptions of known routes. For example, 4-phenylthiophenol is prepared from 4-bromophenol and cuprous thiophenol by the reaction of Adams [R. Adams, W. Reitschneider and N. D. Neir, Croat. Chem. Acta. 29, 277 (1957)] or from phenol and phenylsulfenyl chloride by the method of Lecher [H. Lecher et al., Chem. Ber., 58; 409 (1925) ]. Modification of the Lecher method by substituting 3-methoxyphenol or m-cresol for phenol yields 3-methoxy-4-phenylthiophenol and 3-methyl-4-phenylthiophenyl respectively. The phenolic sulfoxides or sulfones can be prepared by oxidation of the corresponding sulfides by standard methods. For example, 4-phenylthiophenol can be converted to the sulfoxide by oxidation with sodium metaperiodate in aqueous methanol at ambient temperatures or converted to the sulfone by oxidation with hydrogen peroxide in refluxing acetic acid.

The O,S-dialkyl phosphorochloridothiolates are also known in the literature and are prepared by reacting an alkylsulfenyl chloride with a dialkyl chlorophosphite [A. F. Lippman, J. Org. Chem., 30, 3217 (1965) ].

The following examples are given by way of illustration and are not be considered as limitations of the present invention.

Examples 1 to 25 are illustrative preparations of starting materials useful in the synthesis of compounds of this invention. The remaining Examples 26–30, 32–34, 36–38, 43, 45, 48, 52 and 53 are illustrative preparations of compounds listed in Table I below.

EXAMPLE 1

Preparation of S-sec-butyl O-ethyl phosphorochloridothiolate

Sulfuryl chloride, 6.90 g. (0.05 mole) is added dropwise to a −5° to −10° C. solution of sec-butyl disulfide, 8.90 g. (0.05 mole), and 50 ml. of carbon tetrachloride over an approximate 10 minute period. The mixture is brought slowly to room temperature and stirred for 30 minutes until the liberation of sulfur dioxide subsides. This sec-butyl sulfenyl chloride solution is then added dropwise over a 15 minute period to a solution of diethyl chlorophosphite, 15.6 g. (0.1 mole) and 50 ml. of carbon tetrachloride at 5° C. The reaction is then brought slowly to room temperature and stirred for 30 to 60 minutes. The carbon tetrachloride is removed by vacuum stripping and the residue fractionally distilled in vacuo. The middle faction, distilling at 85° C/0.1 mm., is 18.0 g. (83% theory) of the desired product. Analysis calculated (found) for $C_6H_{14}ClO_2PS$: C, 33.12 (33.57); H, 6.53 (6.71); P, 14.29 (14.26); S, 14.80 (14.95).

EXAMPLES 2 – 6

In a manner similar to that of Example 1, the following compounds are likewise readily prepared:
O-ethy S-n-propyl phosphorochloridothiolate
b.p. 75° C/ 0.1 mm
S-n-butyl O-ethyl phosphorochloridothiolate
b.p. 75°–80° C/ 0.2 mm
O-ethyl S-isobutyl phosphorochloridiothiolate
b.p. 74° C/ 0.2 mm
O-ethyl S-n-pentyl phosphorochloridothiolate
b.p. 100° C/ 0.15 mm
O-ethyl S-isopentyl phosphorochloridothiolate
b.p. 100° C/ 0.1 mm

EXAMPLE 7

Preparation of 3-methyl-4-phenylthiophenol

To a solution of carbon tetrachloride saturated with chlorine is added dropwise, 40.0 g. (0.36 mole) of thiophenol over a period of 60 minutes at 15° C.; a slow stream of chlorine is bubbled into the solution simultaneously. At the conclusion of the thiophenol addition, the chlorine addition is halted. The red-orange solution is held at room temperature for an additional hour and then concentrated to give a quantitative yield of phenyl sulfenyl chloride.

To a solution of 22.4 g. (0.21 mole) of m-cresol in 100 ml. of carbon tetrachloride is added dropwise with stirring, 30.0 g. (0.21 mole) of phenyl sulfenyl chloride at 0°–5° C. over a period of 30 minutes. The light pink solution is stirred overnight at room temperature and then concentrated in vacuo to give 44.8 g. of the impure phenol. The crude product is taken up in 100 ml. of 10% sodium hydroxide, and extracted twice with 50 ml. portions of ether, which are discarded. The basic solution is neutralized with concentrated hydrochloric acid and then extracted twice with 50 ml. portions of chloroform. The organic extracts are combined, dried over sodium sulfate and concentrated in vacuo to give 34.9 g. of yellow oil. Fractional distillation yields 19.9 g. (b.p. 125°–135° C / 0.1 mm) of the desired phenol.

EXAMPLES 8 – 9

In a manner similar to that of Example 7, the following compounds are likewise readily prepared:
4-phenylthiophenol, b.p. 139°–148° C/0.1 mm
3-methoxy-4-phenylthiophenol, b.p. 126°–133° C/0.1 mm

EXAMPLE 10

Preparation of 4-(4'-chlorophenylthio)-3-chlorophenol and 2-(4'-chlorophenylthio)-5-chlorophenol To a slurry of 33.4 g. (0.25 mole) of N-chlorosuccinimide in 400 ml. of carbon tetrachloride, stirring at 10° C., is added dropwise a solution of 36.2 g. (0.25 mole) of p-chlorothiophenol in 50 ml. of carbon tetrachloride over a period of 1 ¼ hours. The slurry is held at room temperature overnight and then filtered to remove succinimide. The filtrate, containing approximately 45 g. (0.25 mole) of p-chlorophenylsulfenyl chloride, is added dropwise over a two hour period, at 3°–5° C., to a stirring solution of 41.6 g. (0.325 mole) of 3-chlorophenol in 100 ml. of carbon tetrachloride. The solution is held overnight at room temperature and the concentrated in vacuo to give 77.9 g. of a brown oil. The crude product is taken up in 200 ml. of 10% sodium hydroxide and extracted twice with 50 ml. of portions of ether, which are discarded. The basic solution is neutralized with concentrated hydrochloric acid and then extracted twice with 50 ml. portions of chloroform. The organic extracts are combined, dried over sodium sulfate and concentrated in vacuo to give 57.3 of the isomeric (chlorophenylthio)-chlorophenols as a brown oil in a 1.1:1 ratio. Fractional distillation gives 27.5 g. (41%) of 2-(4'-chlorophenylthio)-5-chlorophenol (b.p. 148°–50° C./0.05 mm). The pot residue containing the non-distillable isomer is dissolved in benzene, passed through 20 g. of silica gel to remove color, and concentrated in vacuo to give 15.9 g. (24%) of 4-(4'-chlorophenylthio)-3-chlorophenol.

EXAMPLES 11 - 25

In a manner similar to that of Example 10, the following compounds are likewise readily prepared:

| | |
|---|---|
| 4-(4'-chlorophenylthio)phenol | b.p. 188–189° C./ 2.0 mm |
| 2-(4'-chlorophenylthio)phenol | b.p. 150–155° C./ 0.2 mm |
| 4-(3',4'-dichlorophenylthio)phenol | * |
| 2-(3',4'-dichlorophenylthio)phenol | b.p. 145–155° C./ 0.2 mm |
| 4-(4'-fluorophenylthio)phenol | b.p. 135–150° C./ 0.25 mm |
| 4-(2'-nitrophenylthio)phenol | m.p. 84–88° C. |
| 4-chloro-2-(phenylthio)phenol | b.p. 110° C./ 0.25 mm |
| 6-chloro-2-(phenylthio)phenol | b.p. 118° C./ 0.2 mm |
| 2-phenylthio-3-trifluoromethylphenol** | |
| 4-phenylthio-3-trifluoromethylphenol** | b.p. 94° C./0.2 mm |
| 2-phenylthio-4-methylphenol | b.p. 109–111° C./ 0.2 mm |
| 2-phenylthio-4-methoxyphenol | b.p. 123–127° C./ 0.2 mm |
| 4-(4'-chlorophenylthio)-2-methylphenol | m.p. 115–115.5° C. |
| 4-(3'-methylphenylthio)phenol | b.p. 140–145° C./ 0.15 mm |
| 4-(4'-methylphenylthio)phenol | b.p. 149–157° C./ |

| | |
|---|---|
| 2-(4'-methylphenylthio)phenol | 0.05 mm<br>b.p. 142–149° C./<br>0.05 mm |

*Non-distillable oil
**Mixture

EXAMPLE 26

Preparation of O-ethyl O-(4-phenylthiophenyl) S-n-propyl phosphorothiolate

To a solution of 20.0 g. (0.1 mole) of 4-phenylthiophenol in 150 ml. of anhydrous acetonitrile is added, 4.2 g. (0.1 mole) of sodium hydride (57% in mineral oil) portionwise. The slurry is stirred at room temperature until no further hydrogen is evolved and then 20.0 g. (0.1 mole) of O-ethyl S-n-propyl phosphorochloridothiolate is added dropwise with stirring over 45 minutes at 5° C. The slurry is stirred overnight at room temperature, filtered to remove sodium chloride and mineral oil, and concentrated in vacuo to give 35.1 g. (95%) of the desired product as a yellow oil.

The crude product is taken up in 100 ml. of benzene, washed twice with 20 ml. portions of water, dried over sodium sulfate and reconcentrated in vacuo to give 32.0 g. of the desired product as a pale yellow oil.

EXAMPLE 27

Preparation of O-ethyl-O-)3-methyl-4-phenylthiophenyl) S-n-propyl phosphorothiolate To a solution of 6.0 g. (0.028 mole) of 3-methyl-4-phenylthiophenol in 50 ml. of anhydrous acetonitrile is added, 1.2 g. (0.028 mole) of sodium hydride (57% in mineral oil) portionwise. The slurry is stirred at room temperature until no further hydrogen is evolved and then 5.63g. (0.028 mole) of O-ethyl-S-n-propyl phosphorochloridothiolate is added dropwise with stirring over 45 minutes at 5° C. The slurry is stirred overnight at room temperature, filtered to remove sodium chloride and mineral oil, and concentrated in vacuo to give 9.6 g. (89%) of the desired product as a yellow oil.

The crude product is taken up in 100 ml. of benzene, washed twice with 25 ml. portions of water, dried over sodium sulfate and reconcentrated in vacuo to give 7.4 g. of the desired product as a pale yellow oil. The oil is further purified by chromatography on silica gel using acetone/hexane as the eluent. The main fraction, 6.0 g. (56%) is shown by nmr to be the desired product: nmr (CDCl$_3$) =0.90 3H,t, CH$_3$), 1.35 (3H, t, CH$_3$), 1.75 (2H, m, SCH$_2$CHCH$_3$), 2.30 (3H, s, CH$_3$), 2.90 (2H, m, P-SCH$_2$CH$_2$CH$_3$), 4.18 (2H, m, P-OCH$_2$CH$_3$), 7.0 (8H,m,aromatic).

EXAMPLE 28

Preparation of O-ethyl-O-(3-methoxy-4-phenylthiophenyl) S-n-propyl phosphorothiolate To a solution of 10.0 g. (0.043 mole) of 3-methoxy-4-phenylthiophenyl in 100 ml. of anhydrous acetonitrile is added, 1.82 g. (0.044 mole) of sodium hydride (57% in mineral oil) portionwise. The slurry is stirred at room temperature until no further hydrogen is evolved and then 8.0 g. (0.043 mole) of O-ethyl S-n-propyl phosphorochloridothiolate in 50 ml. of acetonitrile is added dropwise with stirring over 45 minutes at 5° C. The slurry is stirred overnight at room temperature, filtered to remove sodium chloride and mineral oil, and concentrated in vacuo to give 14.9 g. (87%) of the desired product as a yellow oil.

The crude product is taken up in 100 ml. of benzene, washed twice with 20 ml. of portions of water, dried over sodium sulfate and reconcentrated in vacuo to give 11.0 g. of the desired product as a pale yellow oil. The oil, 6.0 g., is further purified by chromatography as described in Example 27. The main fraction, 3.6 (52%) is shown by nmr to be the desired product: nmr (CDCl$_3$),δ=0.93 (3H, t, CH$_3$), 1.32 (3H, t, CH$_3$),1.67 (2H, m, SCH$_2$ CH$_2$CH$_3$), 3.92 (3H, s, OCH$_3$), 4.12 (2H, m, OCH$_2$CH$_3$), 6.8-7.5 (8H, m, aromatic).

EXAMPLE 29

Preparation of O-[4-(4'-chloro)phenylthiophenyl]O-ethyl S-n-propyl phosphorothiolate To a solution of 23.7 g. (0.1 mole) of 4-(4'-chloro)-phenylthiophenol in 100 ml. of benzene is added 2.4 g. (0.1 mole) of sodium hydride (mineral oil free) at 8° C. The thick slurry is brought to 50° C. for 15 minutes to complete the hydrogen evolution and recooled to 5° C. Then, 20.2 g. (0.1 mole) of O-ethyl S-n-propyl phosphorochloridothiolate is added dropwise at 8° C. The resulting slurry is held for two days at room temperature and then filtered to remove sodium chloride. The filtrate is washed once with a 500 ml. of portion of water, once with a 250 ml. portion of 2% sodium carbonate, three times with 500 ml. portions of water, and then concentrated in vacuo to give a quantitative yield of the product as a yellow oil. A portion of the oil is purified by chromatography as described in Example 27.

Example 30

Preparation of O-[2-(4'-chlorophenylthio)phenyl]O-ethyl S-n-propyl phosphorothiolate A solution of 30.0 g. (0.127 mole) of 2-(4'-chlorophenyl)-phenol in 50 ml. of benzene is added dropwise to a stirring suspension of 3.25 g. (0.127 mole) of sodium hydride in 50 ml. of benzene at 15°-23° C. The slurry is brought to 45° C., stirred until no further gas is evolved, and then cooled to 5° C. A solution of 25.8 g. (0.127 mole) of O-ethyl S-n-propyl phosphorochloridothiolate in 50 ml. of benzene is added dropwise at 5° C. After stirring overnight at room temperature, the reaction is filtered to remove sodium chloride. The filtrate is washed once with 200 ml. of water, once with 200 ml. of 5% aqueous sodium carbonate, twice with 200 ml. portions of water, and then concentrated in vacuo to give a quantitative yield of the crude phosphorothiolate. A portion of the oil (10 g.) is purified by chromatography as described in Example 27, to give 7.2 g. of the pure phosphorothiolate as a pale yellow oil.

EXAMPLE 32

Preparation of O-ethyl O-[4-(4'-nitrophenylthiophenyl] S-n-propyl phosphorothiolate A suspension of 0.75 g. (0.0313 mole) of sodium hydride in 20 ml. of acetonitrile is added dropwise to a stirring solution of 7.4 g. (0.03 mole) of 4-(4'-nitrophenylthio)phenol in 40 ml. of acetonitrile at 30°-40°

C. The slurry is warmed at 50°–60° C. until no further gas is evolved, and then cooled to 30° C. A solution of 7.4 g. (0.0315 mole) of O-ethyl S-n-propyl phosphorochloridothiolate in 10 ml. of acetonitrile is added dropwise at 30°–35° C. After stirring overnight at room temperature, the reaction mixture is filtered to remove sodium chloride. The filtrate is washed and concentrated as described in Example 30, to give 10.0 g. (78%) of the desired product as a deep yellow oil.

EXAMPLE 33

Preparation of O-[4-(4'-chlorophenylsulfonyl) phenyl] O-ethyl S-n-propyl phosphorothiolate A solution of 10.0 g. (0.037 mole) of 4-(4°-chlorophenylsulfonyl)phenol in 50 ml. of benzene and 100 ml. of ethylenedichloride is added dropwise to a stirring suspension of 0.89 g. (0.037 mole) of sodium hydride in 50 ml. of benzene at 15°–23° C. The slurry is brought to 45° C., stirred until no further gas is evolved, and then cooled to 5° C. A solution of 7.5 g. (0.037 mole) of O-ethyl S-n-propyl phosphorochloridothiolate in 50 ml. of benzene is added dropwise at 5° C. After stirring overnight at room temperature, the reaction mixture is filtered to remove sodium chloride. The filtrate is washed and concentrated as described in Example 30, to give 15.8 g. (99%) of the crude phosphorothiolate. A portion of the oil (10 g.) is further purified by chromatography as described in Example 27 to give 4.5 g. of the pure phosphorothiolate as a pale yellow oil.

EXAMPLE 34

Preparation of O-[4-(4'-chlorophenylsulfinyl)-phenyl]O-ethyl S-n-propyl phosphorothiolate A solution of 10.0 g. (0.043 mole) of 4-(4'-chlorophenylsulfinyl)phenol in 50 ml. of benzene is added dropwide to a stirring suspension of 1.03 g. (0.043 mole) of sodium hydride in 50 ml. of benzene at 15°– ° C. The slurry is brought to 45° C, stirred until no further gas is evolved and then cooled to 5° C. A solution of 8.71 g. (0.043 mole) of O-ethyl S-n-propyl phosphorochloridothiolate in 50 ml. of benzene is added dropwise at 5° C. After stirring overnight at room temperature, the reaction mixture is filtered to remove sodium chloride. The filtrate is washed and concentrated as described in Example 30 to give 13.8 g. (77%) of the desired phosphorothiolate.

EXAMPLE 36

Preparation of O-Methyl O-[4-(4'-nitrophenylthio)phenyl] S-n-propyl Phosphorothiolate A solution of 7.98 g. (0.033 mole) of 4-(4'-nitrophenylthio)phenol in 20 ml. of acetonitrile is added dropwise to a stirring suspension of 0.80 g. (0.033 mole) of sodium hydride in 50 ml. of acetonitrile at 23°–33° C. The slurry is warmed to 50° C. until no more gas is evolved, and then 6.30 g. (0.033 mole) of O-methyl S-n-propyl phosphorochloridothiolate in 10 ml. of acetonitrile is added dropwise at 33°–38° C. The temperature is maintained at 45° C. overnight and then the reaction mixture is filtered to remove sodium chloride. The filtrate is washed and concentrated as described in Example 30 to give 9.9 g. (74%) of the phosphorothiolate as a yellow-orange oil.

EXAMPLE 37

Preparation of O-[3-chloro-4-(4'-chlorophenylthio)phenyl] O-ethyl S-n-propyl phosphorothiolate A solution of 8.22 g. (0.03 mole) of 3-chloro-4-(4'-chlorophenylthio)phenol in 60 ml. of acetonitrile is added dropwise to a stirring suspension of 0.73 g. (0.03 mole) of sodium hydride in 100 ml. of acetonitrile at 20°–30° C. The slurry is warmed to 40° C., maintained at that temperature until there is no further evolution of hydrogen gas, and then cooled to room temperature. A solution of 6.16 g. (0.03 mole) of O-ethyl S-n-propyl phosphorochloridothiolate in 10 ml. of acetonitrile is added dropwise to the stirring suspension at 27°–32° C. After stirring overnight at room temperature, the reaction mixture is filtered to remove sodium chloride, and the filtrate concentrated in vacuo to give 12.5 g. (94%) of the phosphorothiolate as an orange oil. A portion of the oil is further purified by chromatography as described in Example 27 to give the product as a pale yellow oil.

EXAMPLE 38

Preparation of O-ethyl O-[2-methyl-4-(4'-chlorophenylthio)phenyl] S-n-propyl phosphorothiolate A solution of 8.0 g. (0.032 mole) of 2-methyl-4-(4'-chlorophenylthio)phenol in 60 ml. of acetonitrile is added dropwise to a stirring suspension of 0.77 g. (0.032 mole) of sodium hydride in 100 ml. of acetonitrile at 20°–30° C. The slurry is warmed to 40° C., maintained at that temperature until there is no further evolution of hydrogen gas, and then cooled to room temperature. A solution of 6.5 g. (0.032 mole) of O-ethyl S-n-propyl phosphorochloridothiolate in 10 ml. of acetonitrile is added dropwise to the stirring suspension at 27°–32° C. After stirring overnight at room temperature, the reaction mixture is filtered to remove sodium chloride and the filtrate concentrated in vacuo to give 13.0 g. (98%) of the phosphorothiolate as an orange oil. A portion of the oil is further purified by chromatography as described in Example 27 to give the product as a pale yellow oil.

EXAMPLE 43

Preparation of O-[2-(4'-chlorophenylthio)-5-chlorophenyl] O-ethyl S-n-propyl phosphorothiolate To a slurry of 0.79 g. (0.033 mole) of sodium hydride in 50 ml. of acetonitrile is added dropwise, a solution of 8.93 g. (0.033 mole) of 2-(4'-chlorophenylthio)-5-chlorophenol in 50 ml. of acetonitrile. The solution is stirred until the evolution of hydrogen ceases. Then, 6.64 g. (0.033 mole) of O-ethyl S-n-propyl phosphorochloridothiolate is added dropwise to the solution. The resultant slurry is warmed to 50° C. for one hour and then held for several days at room temperature. The precipitated sodium chloride is removed by filtration and the filtrate concentrated in vacuo to give 13.1 g. (98%) of the desired product as a yellow oil. A portion of the oil is further purified by chromatography as described in Example 27. The structure is confirmed by nmr: $(CDCl_3)$ δ =2.90 $(2H,m,P-SCH_2CH_2CH_3)$ 4.25 (2H, m, $P—OCH_2CH_3$) 7.0–7.8 (7H,m, aromatic).

EXAMPLE 45

Preparation of O-ethyl
O-[4-(2'-nitrophenylthio)phenyl] S-n-propyl
phosphorothiolate To a slurry of 0.50 g. (0.02 mole) of sodium hydride in 50 ml. of acetonitrile is added dropwise, a solution of 5.17 g. (0.02 mole) of 4-(2'-nitrophenylthio)phenol in 50 ml. of acetonitrile. The solution is stirred until the evolution of hydrogen ceases. Then, 4.24 g. (0.02 mole) of O-ethyl S-n-propyl phosphorochloridothiolate in 50 ml. of acetonitrile is added dropwise at room temperature and stirred for an additional 24 hours. The precipitated sodium chloride is removed by filtration and the filtrate concentrated in vacuo to give 8.3 g. of the product as a yellow oil. A portion of the oil is further purified by chromatography as described in Example 27. The structure is confirmed by nmr: (CDCl$_3$) δ =2.95 (2H, m, P-SCH$_2$CH$_2$CH$_3$), 4.35 (2H,m,P-O-CH$_2$CH$_3$) 6.8–8.3 (8H, m, aromatic).

EXAMPLE 48

Preparation of S-sec-butyl
O-[4-(4-chlorophenylthio)phenyl] O-ethyl
phosphorothiolate A suspension of 0.55 g. (0.023 mole) of sodium hydride in 20 ml. of toluene is added dropwise to a stirring solution of 4.54 g. (0.019 mole) of 4-(4'-chlorophenylthio)phenol in 50 ml. of toluene at 25°–30° C. The slurry is warmed to 40°–50° C. for one hour, after which time 4.15 g. (0.019 mole) of S-sec-butyl O-ethyl phosphorochloridothiolate is added dropwise at room temperature. After stirring overnight at room temperature, the reaction mixture is filtered to remove sodium chloride, and the filtrate concentrated in vacuo to give 2.3 g. (29%) of the phosphorothiolate as an orange oil. A portion of the oil is further purified by chromatography as described in Example 27 to give the pure phosphorothiolate.

EXAMPLE 52

Preparation of O-[4-(4'-chlorophenylthio)phenyl]
O-ethyl S-isobutyl phosphorothiolate A suspension of 0.55 g. (0.023 mole) of sodium hydride in 20 ml. of toluene is added dropwise to a stirring solution of 4.54 g. (0.019 mole) of 4-(4'-chlorophenylthio)phenol in 50 ml. of toluene at 25°–30° C. The slurry is warmed to 40°–50° C. for one hour, after which time 4.98 g. (0.023 mole) of O-ethyl S-isobutyl phosphorochloridothiolate is added dropwise at room temperature. After stirring overnight at room temperature, the reaction mixture is filtered to remove sodium chloride, and the filtrate concentrated in vacuo to give 5.5 g. (69%) of the phosphorothiolate as an orange oil. A portion of the oil is further purified by chromatography as described in Example 27 to give the pure phosphorothiolate.

EXAMPLE 53

Preparation of S-n-butyl
O-[4-(4'-chlorophenylthio)phenyl] O-ethyl
phosphorothiolate The reaction is carried out as in Example 52 with the exception that S-n-butyl O-ethyl phosphorochloridothiolate, 4.15 g. (0.019 mole), is used to give 1.1 g. (14%) of the pure phosphorothiolate as a pale yellow oil.

TABLE I

ELEMENTAL ANALYSIS

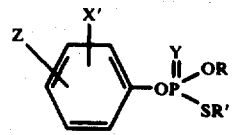

| Ex. No. | Z | Y | X' | R | R' | C | H | P | S |
|---|---|---|---|---|---|---|---|---|---|
| 26 | 4-(φS—) | O | H | C$_2$H$_5$ | C$_3$H$_7$n | 55.5 (55.3) | 5.77 (5.80) | 8.43 (7.14) | 17.4 (17.2) |
| *27 | 4-(φS—) | O | 3-CH$_3$ | C$_2$H$_5$ | C$_3$H$_7$n | | | | |
| *28 | 4-(φS—) | O | 3-CH$_3$O | C$_2$H$_5$ | C$_3$H$_7$n | | | | |
| 29 | 4-(4'-ClφS—) | O | H | C$_2$H$_5$ | C$_3$H$_7$n | 50.1 (50.4) | 5.02 (5.03) | 7.69 (7.33) | 15.9 (15.3) |
| 30 | 2-(4'-ClφS—) | O | H | C$_2$H$_5$ | C$_3$H$_7$n | 50.7 (50.2) | 5.00 (5.17) | 7.69 (7.64) | 15.9 (15.5) |
| 31 | 4-(4'-NO$_2$φS—) | S | H | C$_2$H$_5$ | C$_3$H$_7$n | 47.5 (47.3) | 4.69 (4.85) | — | — |
| 32 | 4-(4'-NO$_2$φS—) | O | H | C$_2$H$_5$ | C$_3$H$_7$n | 49.4 (49.5) | 4.88 (4.71) | — | — |
| 33 | 4-(4'-ClφSO$_2$—) | O | H | C$_2$H$_5$ | C$_3$H$_7$n | 47.3 (47.4) | 4.53 (5.09) | 7.13 (7.21) | 14.8 (14.7) |
| 34 | 4-(4'-ClφSO—) | O | H | C$_2$H$_5$ | C$_3$H$_7$n | 48.8 (47.6) | 4.85 (5.06) | 7.39 (8.00) | 15.3 (15.3) |
| 35 | 4-(4'NO$_2$φS—) | O | H | C$_3$H$_7$n | C$_3$H$_7$n | 50.6 (51.4) | 5.19 (5.21) | 7.25 (6.13) | — |
| 36 | 4-(4'-NO$_2$φS) | O | H | CH$_3$ | C$_3$H$_7$n | 48.1 (47.4) | 4.54 (4.80) | 7.75 (7.95) | 16.1 (16.2) |
| 37 | 4-(4'-ClφS—) | O | 3-Cl | C$_2$H$_5$ | C$_3$H$_7$n | 46.7 (46.8) | 4.38 (4.47) | 7.08 (6.96) | — |
| *38 | 4-(4'-ClφS—) | O | 2-CH$_3$ | C$_2$H$_5$ | C$_3$H$_7$n | | | | |
| 39 | 4-(4'-CH$_3$φS—) | O | H | C$_2$H$_5$ | C$_3$H$_7$n | 56.5 (56.1) | 6.06 (6.10) | 8.10 (7.98) | — |
| 40 | 2-(3',4'-diClφS—) | O | H | C$_2$H$_5$ | C$_3$H$_7$n | 46.7 (46.4) | 4.38 (4.35) | 7.08 (7.26) | 16.61 (16.38) |
| 41 | 4-(4'-FφS—) | O | H | C$_2$H$_5$ | C$_3$H$_7$n | 52.8 (53.2) | 5.22 (5.24) | 8.01 (8.01) | — |
| 42 | 4-(4'-NO$_2$φS—) | O | 2-Br | C$_2$H$_5$ | C$_3$H$_7$n | 41.5 (40.5) | 3.89 (3.87) | 6.29 (5.99) | — |
| *43 | 2-(4'-ClφS—) | O | 5-Cl | C$_2$H$_5$ | C$_3$H$_7$n | | | | |

TABLE I-continued

ELEMENTAL ANALYSIS

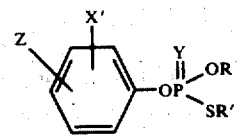

| Ex. No. | Z | Y | X' | R | R' | ANALYSIS CALCULATED (FOUND) C | H | P | S |
|---|---|---|---|---|---|---|---|---|---|
| 44 | 3-(φS—) | O | H | C₂H₅ | C₃H₇n | 55.4 (56.7) | 5.74 (5.90) | 8.41 (7.76) | — |
| *45 | 4-(2'-NO₂φS—) | O | H | C₂H₅ | C₃H₇n | | | | |
| 46 | 2-(φS—) | O | 4-Cl | C₂H₅ | C₃H₇n | 50.7 (51.7) | 5.00 (5.25) | 7.69 (7.51) | — |
| 47 | 2-(φS—) | O | 6-Cl | C₂H₅ | C₃H₇n | 50.7 (52.4) | 5.00 (5.47) | 7.69 (7.87) | — |
| 48 | 4-(4'-ClφS—) | O | H | C₂H₅ | C₄H₉sec | 51.8 (52.0) | 5.32 (5.44) | 7.43 (7.20) | — |
| 49 | 2-(φS—) | O | 4-CH₃ | C₂H₅ | C₃H₇n | 56.5 (54.2) | 6.06 (6.41) | 8.10 (8.75) | — |
| 50 | 4-(3'-CH₃φS—) | O | H | C₂H₅ | C₃H₇n | 56.5 (55.2) | 6.06 (6.26) | 8.10 (8.17) | — |
| 51 | 2-(φS—) | O | 4-CH₃O | C₂H₅ | C₃H₇n | 54.3 (53.9) | 5.82 (6.04) | 7.77 (7.63) | — |
| 52 | 4-(4'-ClφS—) | O | H | C₂H₅ | C₄H₉iso | 51.8 (51.9) | 5.32 (5.52) | 7.43 (7.30) | — |
| 53 | 4-(4'-ClφS—) | O | H | C₂H₅ | C₄H₉n | 51.8 (51.9) | 5.32 (5.38) | 7.43 — | — |

*structure confirmed by nmr

The organophosphorothiolates and phosphorodithioates of this invention possess general utility as arthropodicides, particularly against members of the class Arachnoidea, which includes the order Acarina, as represented by mites and ticks, and Insecta, the insects. Certain compounds of this invention are also active as nematocides, ovicides, larvicides, and fungicides, particularly phytopathogenic fungicides.

Initial evaluations are made on the following mite, insects and nematode:

| Code Symbol | Common Name | Latin Name |
|---|---|---|
| TSM | Two-spotted spider mite | Tetranychus urticae |
| GPA | Green peach aphid | Myzus persicae |
| BB | Mexican bean beetle | Epilachna varivestis |
| AW | Southern armyworm | Spodoptera eridania |
| BW | Boll Weevil | Anthonomus grandis |
| LST | Lone star tick | Amblyoma americanum |
| HF | House fly | Musca domestica |
| SF | Stable fly | Stomoxys calcitrans |
| Nema | Southern root knot nematode | Meloidogyne incognita |

A test solution containing 600 ppm of test compound can be made by dissolving the test compound in a solvent (acetone: methanol, 1:1), adding surfactant and then water to give an acetone:methanol:water system of 10:10:80. A 1:1 mixture of an alkylarylpolyether-alcohol (commercially available under the trademark Triton X-155) and a modified phthalic glycerol alkyd resin (commercially available under the trademark Triton B-1956) can be utilized at the equivalent of one ounce per gallon of test solution as a surfactant.

For the mite test, infested bean (*Phaseolus limeanus*) leaf discs (1.25 inches in diameter) containing about 50 mites and for green peach aphid tests, infested broccoli (*Brassica oleracea italica*) leaves or portions thereof containing about 50 aphids are placed in a Petri dish lid on a moistened piece of cotton. The leaves are then sprayed with the test solution using a rotating turntable. They are held for 24 hours and then the percent kill is determined.

For the bean beetle and armyworm test, detached bean leaves on pieces of moistened filter paper are sprayed as above the mite test in similar dishes and allowed to dry. One such dish is infested with 10 third instar Mexican bean beetle larvae, while another is infested with 10 third instar southern armyworm larvae. The dishes are covered. After holding for 48 hours, the percent kill is obtained.

For the boll weevil and house fly tests, half pint glass canning jars with a screened top are used. Food is supplied for the boll weevil (apple) and for the house fly (sugar water). The test insects consist of 10 adult boll weevils and 20 adult house flies. The jars containing the insects are sprayed using the turntable. The percent kill of boll weevil is determined 48 hours after the application. In the house fly test, a percent knockdown is determined one hour after application, the percent kill after 24 hours.

For the tick test, plastic Petri dish bottoms containing a piece of filter paper are sprayed with the test compounds. After the filter paper dries, a small quantity of water is pipetted into each dish to insure proper humidity. The dishes are then infested with about 50 lone star tick larvae and capped with tight-fitting plastic lids. After holding for 24 hours, the percent kill is obtained.

For the stable fly test, glass Mason half-pint jars with a piece of filter paper covering the bottom of each jar, are infested with 20, 3-5 day old male and female stable flies. Screening, held in place with screw-cap lids, is used to confine the flies. The jars containing the flies are sprayed directly on a turntable sprayer. The flies are held at 80° F. and 55% relative humidity for a one hour knock-down (KD) and 24-hour mortality observation. Results are recorded as the number of flies knocked down or dead per total number.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot after which time 3 cucumber (Cucumis sativus) seeds are planted. About 23 days thereafter, the cucumber plants are removed from the soil and the root system examined for the presence of knots. A total of 25 knots or less is considered as a measure of control.

Table II gives the results of the foregoing biological evaluations.

concentration. Twenty-four hours later, the percent kill is determined.

Table III gives the results of these ovicidal and larvicidal tests.

TABLE III

OVICIDAL AND LARVICIDAL EVALUATIONS
Percent Kill

| Ex. No. | Corn Beetworm at 600 ppm | | Two Spotted Mite at 150 ppm | | Mosquito Larvae |
|---|---|---|---|---|---|
| | 0 | L | 0 | L | 1 ppm. |
| 26 | 0 | 100 | 59 | 100 | 100 |
| 27 | 97 | 100 | 0 | 100 | 100 |

TABLE II

ACARICIDAL, INSECTICIDAL and NEMATOCIDAL DATA
% Control, etc. at 600 ppm.

| Ex. No. | TSM | GPA | BB | AW | BW | LST | HF KD | HF KILLED | SF KD | SF KILLED | Nema* |
|---|---|---|---|---|---|---|---|---|---|---|---|
| 26 | 100 | 100 | 100 | 100 | 80 | 0 | 100 | 100 | 95 | 100 | + |
| 27 | 100 | 100 | 100 | 100 | 80 | 0 | 100 | 100 | 70 | 100 | + |
| 28 | 100 | 100 | 100 | 100 | 100 | 0 | 100 | 100 | 80 | 100 | — |
| 29 | 100 | 100 | 100 | 100 | 100 | 100 | 100 | 100 | 100 | 100 | — |
| 30 | 100 | 100 | 100 | 100 | 100 | 100 | 100 | 100 | 100 | 100 | + |
| 31 | 100 | 100 | 0 | 100 | 100 | 0 | 0 | 100 | 0 | 0 | — |
| 32 | 100 | 100 | 100 | 100 | 100 | 80 | 100 | 100 | 100 | 100 | + |
| 33 | 100 | 100 | 100 | 100 | 100 | 0 | 100 | 100 | 100 | 100 | + |
| 34 | 100 | 99 | 100 | 100 | 100 | 0 | 100 | 100 | 100 | 100 | + |
| 35 | 69 | 100 | 100 | 100 | 80 | 0 | 45 | 90 | 100 | 100 | — |
| 36 | 100 | 100 | 100 | 100 | 0 | 0 | 100 | 100 | 55 | 100 | + |
| 37 | 100 | 100 | 100 | 100 | 60 | 0 | 100 | 100 | 40 | 100 | — |
| 38 | 100 | 100 | 100 | 100 | 100 | 0 | 100 | 100 | 15 | 100 | + |
| 39 | 100 | 100 | 100 | 100 | 80 | 0 | 100 | 100 | 10 | 95 | — |
| 40 | 100 | 100 | 100 | 100 | 100 | 90 | 100 | 100 | 35 | 100 | + |
| 41 | 100 | 100 | 100 | 100 | 100 | 0 | 100 | 100 | 90 | 100 | + |
| 42 | 100 | 100 | 100 | 100 | 80 | 60 | 100 | 100 | 65 | 100 | + |
| 43 | 100 | 100 | 100 | 100 | 100 | 100 | 100 | 100 | 0 | 90 | + |
| 44 | 100 | 100 | 100 | 100 | 100 | 0 | 100 | 100 | 100 | 100 | + |
| 45 | 100 | 100 | 100 | 100 | 100 | 0 | 100 | 100 | 100 | 100 | + |
| 46 | 100 | 100 | 100 | 100 | 100 | 100 | 95 | 100 | 0 | 100 | + |
| 47 | 100 | 100 | 100 | 100 | 100 | 100 | 100 | 100 | 100 | 100 | + |
| 48 | 100 | 100 | 100 | 100 | 100 | 0 | 100 | 100 | 100 | 100 | + |
| 49 | 100 | 100 | 100 | 100 | 40 | 0 | 35 | 100 | 0 | 65 | + |
| 50 | 100 | 100 | 100 | 100 | 80 | 0 | 100 | 100 | 20 | 100 | + |
| 51 | 100 | 100 | 100 | 100* | 80 | NT | 55 | 100 | 0 | 90 | + |
| 52 | 100 | 100 | 100 | 100* | 100 | NT | 100 | 100 | 100 | 100 | — |
| 53 | 100 | 100 | 100 | NT | 100 | NT | 0 | 75 | 0 | 80 | — |

*— + means control
— means no control
*— Percent control at 150 ppm.
NT — Not tested
KD — Knock down Ovicidal and larvicidal tests are conducted on representative compounds of this invention. These compounds demonstrate ovicidal and larvicidal activity.

For mite tests involving the two-spotted mite ova and larvae, bean leaf sections containing about 100 eggs are placed on moistened cotton in a Petri dish and sprayed on the turntable with a 150 ppm test solution. These are held for 6 days and examined under the microscope. Unhatched eggs and dead and live larvae are counted and the percent ovicidal and larvicidal activity are determined.

For tests involving the southern corn rootworm (Diabrotica undecimpunctata howardi) ova and larvae, two layers of 4.25 cm. filter papers are placed in small, Petri dishes, and sprayed on the turntable with a 600 ppm solution of the test compound and air dried. About 100 eggs in about one milliliter of water are pipetted onto the filter paper and the dishes covered. These are held for 6 days and examined under the microscope. The percent kill values for ova and larvae are determined.

For the mosquito larvae test, approximately 20, 3-day old yellow fever mosquito larvae (Aedes aegypti) are introduced into styrofoam cups containing 100 ml. of water which has previously been treated with a test solution of selected compounds so as to give a 1 ppm

| 28 | 91 | 100 | 0 | 100 | 100 |
| 29 | 77 | 100* | 85 | 100 | 100 |
| 30 | 92 | 100 | 85 | 100 | 100 |
| 31 | 0 | 100 | 0 | 0 | 100 |
| 32 | 0 | 100 | 40 | 30 | 100 |
| 33 | 0 | 100 | 0 | 100 | 100 |
| 34 | 71 | 100 | 0 | 75 | 100 |
| 35 | 46 | 100 | 0 | 0 | 100 |
| 36 | 48 | 94 | 91 | 100 | 100 |
| 37 | 0 | 100 | 64 | 100 | 100 |
| 38 | 0 | 100 | 0 | 100 | 100 |
| 39 | 58 | 100 | 85 | 100 | 100 |
| 40 | 49 | 100 | 87 | 100 | 100 |
| 41 | 0 | 100 | 36 | 84 | 100 |
| 42 | 0 | 100 | 0 | 0 | 100 |
| 43 | 0 | 100 | 100 | — | 100 |
| 44 | 45 | 100 | 79 | 87 | 100 |
| 45 | 32 | 100 | 0 | 100 | 100 |
| 46 | 38 | 100 | 0 | 93 | 100 |
| 47 | 56 | 100* | 0 | 90 | 100 |
| 48 | 0 | 93* | 0 | 97 | 100 |
| 49 | 0 | 0* | 0 | 61 | 100 |
| 50 | 0 | 95* | 50 | 98 | 100 |
| 51 | 0 | 94 | NT | NT | 100 |
| 52 | NT | NT | NT | NT | 100 |
| 53 | NT | NT | NT | NT | 100 |

*— 150 ppm
— — data not possible, all eggs destroyed
NT — not tested

Fungicidal evaluation of compounds of this invention is carried out by way of a foliar screening test. The general procedure for the fungicidal test is to take potted plants in proper condition of growth for susceptibility to the plant diseases to be evaluated, to spray these on a moving belt and allow them to dry. The plants are then inoculated with the respective fungal spores and allowed to incubate until the disease symptoms and the disease control are read or estimated. Percentage of disease control is recorded.

Compounds of the present invention are tested at a concentration of 300 ppm in a solution or suspension made by dissolving a weighed amount of the candidate fungicide in a 50:50 mixture of acetone and methanol and then adding an equal volume of water.

Some of the plant diseases controlled by compounds of this invention include the following:

| Code Symbol | Common Name | Latin Name |
|---|---|---|
| BPM | Bean Powdery Mildew | Erysiphe polygoni |
| GDM | Grape Downy Mildew | Plasmopara viticola |
| RB | Rice Blast | Piricularia oryzae |
| TLB | Tomato Late Blight | Phytophthora infestans |
| WLR | Wheat Leaf Rust | Puccinia recondita |

Table IV gives the results of the foregoing fungicidal evaluations.

TABLE IV

FUNGICIDAL DATA
Control* at 300 ppm

| Ex. No. | BPM | GDM | RB | TLB | WLR |
|---|---|---|---|---|---|
| 26 | A | B | E | E | E |
| 27 | B | B | B | E | E |
| 28 | E | B | E | B | B |
| 29 | A | E | E | E | A |
| 30 | E | B | A | E | A |
| 31 | E | E | E | E | E |
| 32 | E | A | A | E | E |
| 33 | E | B | B | E | E |
| 34 | E | B | B | E | E |
| 36 | B | E | B | E | NT |
| 38 | A | E | B | E | NT |
| 40 | E | E | B | E | NT |
| 41 | E | A | A | E | NT |
| 42 | E | E | A | E | NT |
| 43 | E | B | A | E | NT |
| 44 | E | E | B | E | E |
| 46 | A | E | A | E | NT |
| 49 | E | E | A | E | NT |
| 50 | C | E | A | E | NT |
| 51 | E | E | A | E | NT |
| 52 | C | E | B | E | NT |

*Disease Rating
A = 97–100% control
B = 90–96% control
C = 70–89% control
D = 50–69% control
E = <50%
NT = not tested The compounds of the present invention are used for protection of plants and animals, including man, from the ravages of harmful and annoying pests or disease organisms which they may carry. The term "pest" as used herein is intended to include arthropods, such as insects and acarids in all stages of development, nematodes, fungi, such as phytopathogenic fungi, and the like. Generally, control of a living organism is achieved in accordance with this invention by application of the compounds in pesticidally effective amounts either directly to the pests to be controlled or to the loci to be freed of or protected from attack by such pests. For example, food, fiber, forage, forest, and ornamental crops and stored products thereof would represent plant protection loci. Treatment with compounds of this invention of domestic aminals, man and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

For use as pesticides the compounds of this invention can be used as solutions in organic solvents or formulations. For example, they can be formulated as wettable powders, emulsifiable concentrates, dusts, granular formulations or flowable emulsifiable concentrates. In such formulations, the organophosphorothiolates or phosphorodithioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The organophosphorothiolate or phosphorodithioate can be taken up on or mixed with a finely particled solid carrier, as for example, clays, inorganic silicates, carbonates, and silicas. Organic carriers can also be employed. Dust concentrates are commonly made wherein organophosphorothiolates or phosphorodithioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable power formulations are made by incorporating the compounds of this invention in an inert, finely divided solid carrier along with a surfactant which can be one or more emulsifying, wetting, dispersing or spreading agents or blend of these. The organophosphorothiolates or phosphorodithioates are usually present in the range of about 10 to about 80% by weight and surfactants form about 0.5 to about 10% by weight.

One convenient method for preparing a solid formulation is to impregnate the organophosphorothiolate or phosphorodithioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving organophosphorothiolates or phosphorodithioates of this invention is an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed.

The surfactants useful as emulsifying agents can constitute about 0.5 to about 10% by weight of emulsifiable concentrate and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. Usually, this will involve the application of the organophosphorothiolate or phosphorodithioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form on substantially soluble in higher boiling solvents.

The application rate will, of course, vary depending upon the purposes for such application, the organophosphorothiolates or phosphorodithioates being utilized, the frequency of dissemination and the like.

By "agronomically acceptable carrier" is meant any substance which can be utilized to dissolve, disperse or diffuse the chemical incorporated therein without impairing the effectiveness of the toxic agent and which does no permanent damage to such environment as soil, equipment and agronomic crops.

Many of the above formulations can be utilized on animals for control of parasites.

For use as insecticides and acaricides, dilute sprays can be applied at concentrations of about 0.001 to about 20 pounds of the active organophosphorothiolate or phosphorodithioate ingredient per 100 gallons of spray. They are usually applied at about 0.01 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a nematocide or as a soil insecticide, the organophosphorothiolates or phosphorodithioates can be applied as a solid formulation, preferably a granular formulation, by broadcasting, side-dressing, soil incorporation or seed treatment. The application rate can be from about 1 to about 50 pounds per acre. For soil incorporation, the compounds of this invention can be mixed with the soil at a rate of about 2 to about 100 ppm.

For use as a fungicide, the organophosphorothiolates or phosphorodithioates can be applied as fungicidal sprays by methods commonly employed, such as conventional highgallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to 50 lbs. per acre of the active ingredient. As a fungicidal seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

What is claimed is:

1. A compound of the formula:

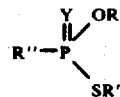

wherein
Y is oxygen or sulfur;
R is $(C_1-C_4)$ alkyl;
R' is $(C_3-C_8)$ alkyl; and
R'' is a group of the formula:

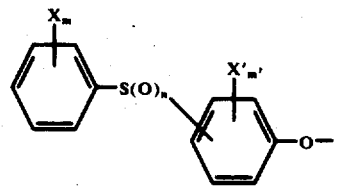

wherein
X is halogen, nitro, trifluoromethyl, $(C_1-C_8)$ alkyl, or $(C_1-C_8)$ alkoxy;
X' is halogen, trifluoromethyl, $(C_1-C_8)$ alkyl or $(C_1-C_8)$ alkoxy;
m and m' are the same or different and are integers from 0 to 3; and
n is an integer from 0 to 2.

2. A compound according to claim 1 wherein R is ethyl, and R' is a $(C_3-C_8)$ alkyl group of the formula:

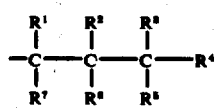

wherein $R^1-R^7$ are individually hydrogen, methyl or ethyl.

3. A compound according to claim 2 wherein Y is oxygen.

4. A compound according to claim 3 wherein R' is n-propyl.

5. A compound according to claim 4 wherein
X is halogen, nitro or methyl;
X' is halogen, methyl or methoxy;
m is an integer from 0 to 2, and
m' is an integer from 0 to 1; and the
R'' group is in a position which is ortho or para to the phophorothiolate group.

6. A compound according to claim 5 wherein n is zero.

7. A compound according to claim 1 wherein m is the integer one.

8. A compound according to claim 1 wherein m is the integer two.

9. A compound according to claim 1 wherein *m* is the integer three.

10. A compound according to claim 7 wherein Y is an oxygen atom.

11. A compound according to claim 10 wherein *m'* is the integer zero.

12. A compound according to claim 10 wherein *m'* is the integer one.

13. A compound according to claim 10 wherein *m'* is the integer two.

14. A compound according to claim 6 having the formula:

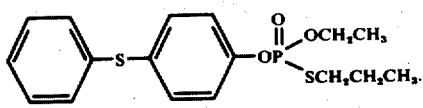

15. A compound according to claim 6 having the formula:

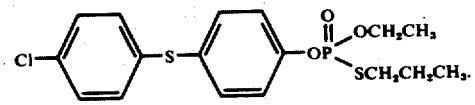

16. A compound according to claim 6 having the formula:

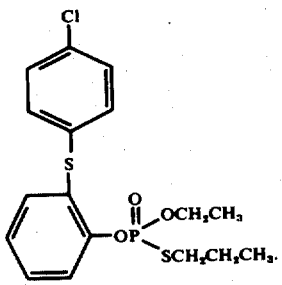

17. A compound according to claim 6 having the formula:

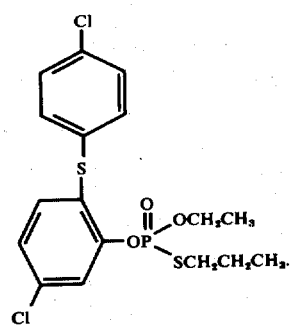

18. A compound according to claim 6 having the formula:

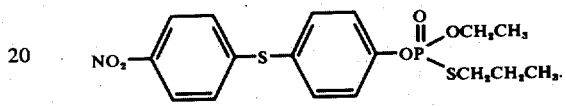

19. A pesticidal composition comprising a pesticidally effective amount of compound according to claim 1 and an agronomically acceptable carrier.

20. A pesticidal composition comprising a pesticidally effective amount of compound according to claim 5 and an agronomically acceptable carrier.

21. A method of controlling pests which comprises applying directly to the pests or to the loci to be freed of or protected from attack by such pests, a pesticidally effective amount of the composition of claim 19.

22. A method of controlling pests which comprises applying directly to the pests or to the loci to be freed of or protected from attack by such pests, a pesticidally effective amount of the compound of claim 1.

23. A method according to claim 21 wherein the pests are acarids, insects, nematodes or phytopathogenic fungi.

24. A method according to claim 23 wherein the pests are acarids or insects.

25. A method according to claim 23 wherein the pests are nematodes.

26. A method according to claim 23 wherein the pests are phytopathogenic fungi.

* * * * *